(12) United States Patent  
Somani et al.

(10) Patent No.: US 7,738,176 B2  
(45) Date of Patent: *Jun. 15, 2010

(54) LENSLET ARRAY FOR BEAM HOMOGENIZATION

(75) Inventors: Seema Somani, Milpitas, CA (US); Charles Munnerlyn, San Jose, CA (US); Mark Arnoldussen, San Carlos, CA (US); John Osborn, Spencerport, NY (US)

(73) Assignee: AMO Manufacturing USA LLC., Santa Ana, CA (US)

( * ) Notice: Subject to any disclaimer, the term of this patent is extended or adjusted under 35 U.S.C. 154(b) by 40 days.

This patent is subject to a terminal disclaimer.

(21) Appl. No.: 12/121,475

(22) Filed: May 15, 2008

(65) Prior Publication Data

US 2009/0122411 A1 May 14, 2009

Related U.S. Application Data

(63) Continuation of application No. 11/683,963, filed on Mar. 8, 2007, now Pat. No. 7,394,595, which is a continuation of application No. 10/913,952, filed on Aug. 6, 2004, now Pat. No. 7,206,132.

(51) Int. Cl.  
*G02B 27/10* (2006.01)

(52) U.S. Cl. .............. 359/619; 359/624; 359/628; 351/221

(58) Field of Classification Search ......... 359/618–628; 349/61–63, 95; 351/205, 221  
See application file for complete search history.

(56) References Cited

U.S. PATENT DOCUMENTS

| | | |
|---|---|---|
| 3,988,066 A | 10/1976 | Suzuki et al. |
| 4,547,037 A | 10/1985 | Case |
| 4,733,944 A | 3/1988 | Fahlen et al. |
| 4,911,711 A | 3/1990 | Telfair et al. |
| 5,016,149 A | 5/1991 | Tanaka et al. |
| 5,041,862 A | 8/1991 | Rossman et al. |
| 5,095,386 A | 3/1992 | Scheibengraber |
| 5,281,211 A | 1/1994 | Parel et al. |

(Continued)

FOREIGN PATENT DOCUMENTS

EP   0 296 982   12/1988

(Continued)

OTHER PUBLICATIONS

Arnoldussen, Mark, "Comparison of Beam Homogenizers for use in a Refractive Laser Surgical System," Proceedings of the 23rd International Congress on Applications of Lasers and Electro-Optics, (2004).

(Continued)

*Primary Examiner*—Huy K Mai

(57) ABSTRACT

Apparatus for homogenizing a laser beam includes a lenslet array. In some embodiments, the lenslets have a negative power. The lenslet array may include from 16 to 36 effective lenslets in some embodiments, or any other suitable number in alternative embodiments. Some embodiments additionally include a re-focusing lens for directing the beamlets onto a target so that the beamlets overlap and the energy distribution is homogenized. In an alternative embodiment, the lenslet array and re-focusing lens are combined in one optic.

20 Claims, 3 Drawing Sheets

U.S. PATENT DOCUMENTS

| | | |
|---|---|---|
| 5,376,086 A | 12/1994 | Khoobehi et al. |
| 5,610,733 A | 3/1997 | Feldman et al. |
| 5,646,791 A | 7/1997 | Glocker |
| 5,912,775 A | 6/1999 | Glocker |
| 6,090,100 A | 7/2000 | Hohla |
| 6,149,643 A | 11/2000 | Herekar et al. |
| 6,159,205 A | 12/2000 | Herekar et al. |
| 6,497,701 B2 | 12/2002 | Shimmick et al. |
| 6,592,574 B1 | 7/2003 | Shimmick et al. |
| 6,605,796 B2 | 8/2003 | Brandinger et al. |
| 6,638,271 B2 | 10/2003 | Munnerlyn et al. |
| 7,206,132 B2 | 4/2007 | Somani et al. |
| 7,394,595 B2 | 7/2008 | Somani et al. |
| 2004/0028175 A1 | 2/2004 | Antoni et al. |
| 2004/0036977 A1 | 2/2004 | Tanaka et al. |
| 2007/0146891 A1 | 6/2007 | Somani et al. |

FOREIGN PATENT DOCUMENTS

| | | | | |
|---|---|---|---|---|
| JP | 6-118204 | * | 4/1994 | ............ 359/619 |
| JP | 62-80617 | | 8/1999 | |
| WO | WO 99/39410 | | 8/1999 | |

OTHER PUBLICATIONS

Foley et al., "Polymer Fly's Eye Light Integrator Lens Arrays for Digital Projectors," Proceedings of the Society for Information Display (2000).

Optics: Special Lenses. [online]. A.W.I. Industries, [retrieved on May 30, 2003]. Retrieved from the Internet: <URL: http://ourworld.compuserve.com/homepages/awi_industries/Optic_special.htm>.

* cited by examiner

LENSLET ARRAY FOR BEAM HOMOGENIZATION

CROSS-REFERENCES TO RELATED APPLICATIONS

This application is a continuation of U.S. patent application Ser. No. 11/683,963 filed Mar. 8, 2007, which application is a continuation of U.S. patent application Ser. No. 10/913,952 filed Aug. 6, 2004 (now U.S. Pat. No. 7,206,132); the full disclosures of which are incorporated herein by reference.

BACKGROUND OF THE INVENTION

The present invention relates generally to laser beam delivery systems. More specifically, the invention relates to devices, systems and methods for homogenizing a laser beam for use in refractive surgery.

Laser beam delivery systems designed to improve the temporal and spatial characteristics of collimated beams of radiation with non-symmetrical energy profile cross sections are known. Some systems, for example, are used to deliver excimer laser beams for performing refractive surgery. In the STAR™ System, developed by VISX, Incorporated (Santa Clara, Calif.), a collimated laser beam used for photorefractive keratectomy (PRK) and phototherapeutic keratectomy (PTK) is delivered to the plane of surgery by means of an optical beam delivery system which provides both spatial and temporal integration for an excimer laser beam. In this system, a collimated laser beam is passed through a set of six prisms surrounding an open path to divide the incoming beam into seven beamlets. Further averaging in the temporal domain is performed by rotating the beam with a rotating telescope. The combination of beam splitting and rotation produces a laser beam having an intensity profile that may be used for refractive surgery. Such a system is described in U.S. Pat. Nos. 5,646,791 and 5,912,775, which are assigned to the assignee of the present invention and which are hereby incorporated fully by reference.

While highly effective in providing spatial and temporal integration to a collimated laser beam, this arrangement sometimes provides beamlets with minor non-uniformities, thus resulting in a laser beam having a slightly varied cross-sectional intensity profile at an ablation target. In other words, such an arrangement may provide less laser beam homogenization (or intensity profile averaging) than would be optimal. One solution would be to increase the number of prisms in the homogenization device, but such a device would be difficult to manufacture. Additionally, transmission of optics exposed to excimer lasers deteriorates with time, and this effect is especially large in relatively thick prism elements. Another disadvantage of a system as described in U.S. Pat. Nos. 5,646,791 and 5,912,775 is that alignment of the system can be relatively challenging.

Therefore, a need exists for improved laser beam homogenizing devices, systems and methods. Such devices, systems and methods would ideally provide for enhanced laser beam intensity averaging and homogenization, thus reducing or eliminating variations in intensity over a cross-section of a laser beam. Ideally, beamlets in such a system would be collimated. Also ideally, devices for homogenizing a laser beam would be relatively simple to produce, would provide for enhanced transmission of light and would be relatively resistant to wear and tear. At least some of these objectives will be met by the present invention.

BRIEF SUMMARY OF THE INVENTION

The present invention generally provides devices, systems and methods including a lenslet array for homogenizing a laser beam. In one aspect of the invention, apparatus for altering an energy distribution across a laser beam comprises an array of negative power lenslets. In some embodiments, for example, the lenslet array comprises a square grid of at least 16 lenslets at least partially within the beam. For example, in some embodiments each lenslet of the lenslet array has a cross-sectional dimension of between about 2 mm and about 5 mm. The lenslet array may have any suitable shape or configuration, but in one embodiment the array comprises a hexagonal grid. Although any other suitable material may be used, in one embodiment the lenslet array comprises fused silica.

In some embodiments, the lenslet array includes a first side comprising a first linear array of concave cylindrical surfaces and a second side opposite the first side and comprising a second linear array of concave cylindrical surfaces extending perpendicular to the surfaces of first linear array. Some embodiments further include a drive for rotating the lenslet array about a longitudinal axis extending along the laser beam.

In another aspect of the invention, apparatus for homogenizing an energy distribution across a laser beam includes a lenslet array for transmitting the laser beam as multiple beamlets, each lenslet having an effective negative power and at least one re-focusing lens for directing the beamlets onto a target so that the beamlets overlap and the energy distribution is homogenized. Optionally, the apparatus may further include at least one rotating member for rotating the lenslet array about a longitudinal axis of the laser beam. In some embodiments, the lenslet array comprises multiple negative power lenslets. In various embodiments, the lenslet array may have any of the features described above.

In some embodiments, the lenslets are rotationally offset between firing laser pulses to account for coupling effects between a laser source and a geometry of the array. In some embodiments, the lenslet array comprises fused silica. Also in some embodiments, the lenslet array comprises a first side comprising a first linear array of concave cylindrical surfaces and a second side opposite the first side and comprising a second linear array of concave cylindrical surfaces extending perpendicular to the surfaces of first linear array. In some embodiments, the re-focusing lens comprises a positive power lens.

Optionally, the apparatus may further include a drive for rotating the lens about a longitudinal axis extending along the laser beam. In some embodiments, the apparatus also includes an aperture disposed at a plane where the combined beamlets overlay to size a beam passing through the aperture. Optionally, the apparatus may further include a telescope to adjust a cross-sectional area of the laser beam before the laser beams arrives at the lenslet array. In some embodiments, the telescope has a fixed position relative to the laser beam.

In another aspect of the present invention, a system for providing a laser beam having a homogenized energy distribution to an eye of a patient includes a source of laser energy, a lenslet array for transmitting the laser beam as multiple beamlets, each lenslet having an effective negative power, and at least one re-focusing lens for directing the beamlets onto a target so that the beamlets overlap and the energy distribution is homogenized. The lenslet array and re-focusing lens may include any of the features described above.

Optionally, the system may further include a drive for rotating the lenslet array about a longitudinal axis extending along the laser beam. The system may further include an aperture disposed at a plane where the combined beamlets overlap to size a beam passing through the aperture. In some embodiments, the system includes a telescope to adjust a cross-sectional area of the laser beam upstream of the lenslet array.

In another aspect of the present invention, a system for providing a laser beam having a homogenized energy distribution to an eye of a patient includes a laser providing a laser beam having unequal divergence in two perpendicular axes, a negative powered lenslet array for transmitting the laser beam as multiple beamlets, the lenslet array comprising opposed surfaces of crossed concave cylindrical surfaces, a drive for rotating the lenslet array about a longitudinal axis extending along the laser beam, and at least one lens for directing the beamlets onto a target so that the beamlets overlap and the energy distribution is homogenized. In this aspect of the invention, the system is configured to fire the laser when the lenslet array is rotated away from 90° and 0° for an excimer laser. The excimer laser has an asymmetrical beam shape, which can be used to define an axis of rotation.

In another aspect of the present invention, a method for homogenizing an energy distribution across a laser beam includes passing a laser beam through a lenslet array to transmit the laser beam as multiple beamlets and directing the beamlets onto a target using at least one lens, so that the beamlets overlap and the energy distribution is homogenized. In some embodiments, the lenslet array comprises a negative power lenslet array, and passing the beam through the lenslet array forms diverging beamlets. Some embodiments involve passing the laser beam through the lenslet array to generate at least 16 beamlets.

Optionally, the method may further include rotating the lenslet array about a longitudinal axis extending along the laser beam. In some embodiments, for example, the lenslet array rotates such that each pulse of a pulsed laser beam passes through the array in an angular window of acceptance about 45° diagonal axes, thus avoiding 0° and 90° orientations of the array relative to the laser beam. In one embodiment, the angular window of acceptance comprises a range of 10° on both sides of the 45° diagonal axes. The method may optionally further include rotating the lens about the longitudinal axis.

In some embodiments, the method further involves adjusting a cross-sectional dimension of the laser beam by passing the beam through a telescope before passing the beam through the lenslet array. In some embodiments, directing the beamlets onto a target involves focusing the beamlets on an aperture disposed apart from the lens. Optionally, the method may further involve directing at least some of the beamlets through an aperture. In some embodiments, directing the beamlets through the aperture may cause the beamlets to arrive collimated at an ablation plane. Also in some embodiments, a cross-sectional dimension of the aperture is selected to provide the laser beam with a desired cross-sectional dimension at an ablation plane.

In another aspect of the present invention, a method of providing a laser beam having a homogenized energy distribution to an eye of a patient involves passing a laser beam through a lenslet array to transmit the laser beam as multiple beamlets, directing the beamlets through at least one lens, so that the beamlets overlap and the energy distribution is homogenized, and directing at least some of the beamlets through an aperture. Various embodiments of this method may include any of the features described above.

These and other aspects of the invention are described in greater detail below, with reference to the drawing figures.

DETAILED DESCRIPTION OF THE INVENTION

Figure 1A:
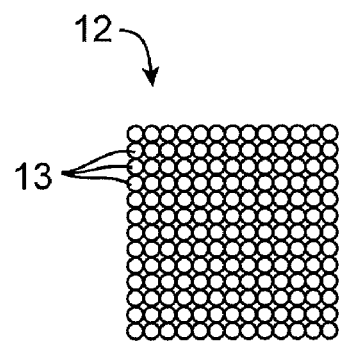
FIG. 1A is an end-on view of a lenslet array according to one embodiment of the present invention; is a schematic sectional view taken along lines 2-2 of FIG. 1 of a portion of the spatial beam integrator.
Figure 1:
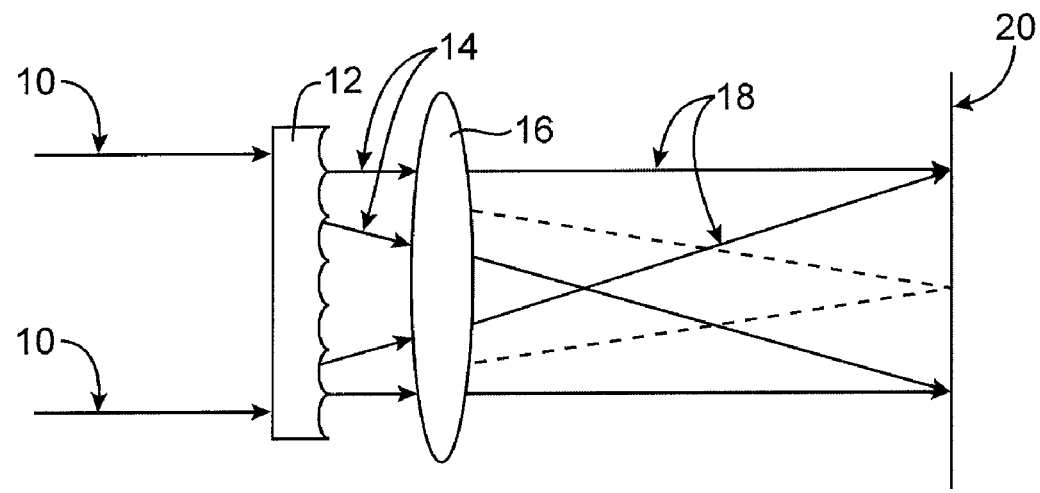
FIG. 1 is a schematic side-view diagram of a portion of a laser beam optical delivery system incorporating one embodiment of the invention.

Turning now to the drawings, FIG. 1 illustrates in schematic form a laser beam delivery apparatus according to the invention. As seen in this figure, a collimated beam 10 from a laser source (not shown) is directed onto the inlet face of a lenslet array 12. Lenslet array 12 divides the beam 12 into multiple beamlets 14, which then pass through a re-focusing lens 16. The refocused beamlets 18 then pass through an aperture 20, adapted for sizing the beamlets and providing a desired cross-sectional beam profile.

Referring to FIG. 1A, the lenslet array 12 may have any suitable number and configuration of lenslets 13. In some embodiments, the lenslet array 12 comprises a square grid of lenslets 13, as shown, with at least 16 lenslets configured to be disposed within the path of a laser beam 10. In other embodiments, however, any other suitable number of lenslets 13 may be included and disposed such that the laser beam 10 passes through all or a portion of them. Furthermore, the size, geometry and configuration of the lenslets 13, and/or 12 the lenslet array 12 may vary in different embodiments. In one embodiment, for example, the lenslet array 12 and the lenslets 13 may both be hexagonal. In another embodiment, as described further below in reference to FIGS. 2A and 2B, the lenslet array 12 may comprise two opposing surfaces of multiple half-cylinders. Lenslets 13 may also have any suitable optical power (focal length). The characteristics of size, shape, geometry, optical power and the like of both the individual lenslets 13 and the lenslet array 12 may be selected, in various embodiments, to provide a desired beam profile at the ablation plane. In one embodiment, for example, the lenslet array 12 includes 16 effective lenslets 13, arranged in a 4×4 square grid, and each lens is about 4.5 mm square, with a focal length of about f=−123.5 mm. Other embodiments may include from 16 to 36 effective lenslets, or any other suitable number.

The beamlets 14 are combined by means of tilting optics, such as the convex refocusing lens 16, or in alternative embodiments a concave mirror, or other optic element(s). The aperture 20 is positioned at a plane where the beamlets 18 overlap and is adapted to size the beam and discard undesired intensity variation at the edges of the beam. This selectable aperture 20 is then optically imaged onto, or close to, the ablation plane. The size and geometry of the imaged spot at the point where the beamlets 18 overlap is determined by the selection aperture 20 and magnification of the lens 16. The overlap area at the selection aperture 20 depends on the size of each lenslet 13 and the lens power of the re-focusing lens 16, but is limited in uniformity by the divergence in each beamlet 18 at that plane. The divergence of a beamlet 18 is determined by the power of a lenslet 13 and the effective power of the lens 16. Incoming divergence from the laser source may also be considered. While a larger number of lenslets 13 implies better spatial averaging, smaller lenslets 13 also cause higher divergence, thus causing a laser beam profile that is not as uniform and more peaked in shape. In order to fill a desired size of the aperture 20 and still achieve a uniform intensity profile, the size and power of the lenslets 13 may be chosen so as to achieve a compromise between spatial averaging and beamlet divergence.

The lenslet array 12 may be either positive or negative power. The beamlets emitted through a positive power lenslet 12 are converging, while beamlets emitted through a negative power lenslet array 12 are diverging. It may be advantageous to use a negative power lenslet array 12 in some embodiments, in order to avoid unwanted beamlet focusing and resulting "hot spots," where laser fluence is high and excess ozone is created if the laser is an Argon Fluoride Excimer laser.

Figure 2A:
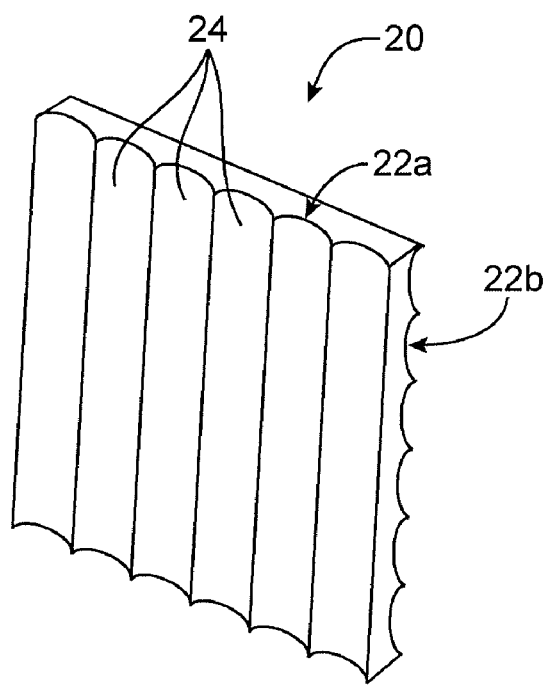
FIGS. 2A and 2B are perspective views of a lenslet array comprising opposed surfaces according to one embodiment of the present invention.
Figure 2B:
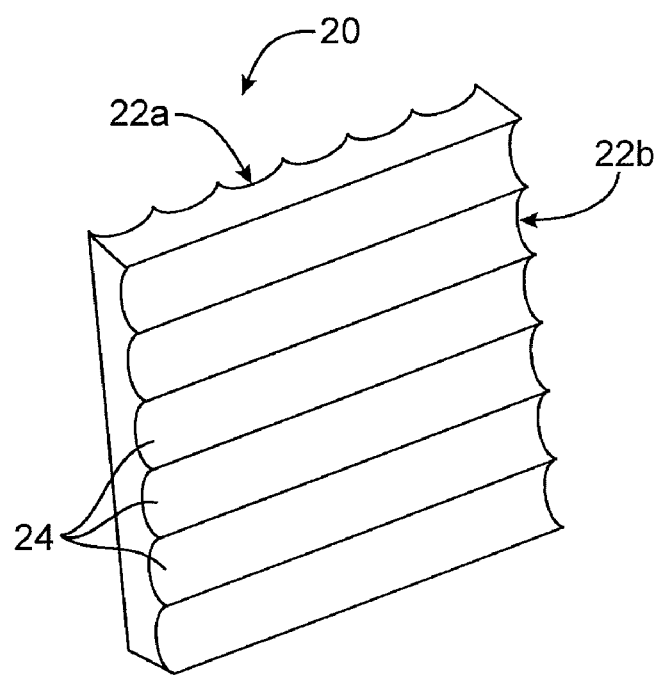

With reference now to FIGS. 2A and 2B, in one embodiment a lenslet array 20 comprises two opposed surfaces 22a, 22b, each surface including multiple partial cylinders 24, arranged in parallel to form multiple concavities. The partial cylinders 24 on one surface 22a, are arranged approximately orthogonally relative to the partial cylinders 24 on the opposed surface 22b. It has been found that opposed surfaces 22a, 22b with oppositely oriented partial cylinders 24 function as lenslets, such as multiple spherical lenslets. Furthermore, a lenslet array 20 as shown is typically easier to manufacture than an alternative array comprising multiple spherical lenslets. For example, the array 20 may be made of fused silica, with the concave partial cylinders 24 etched on the surfaces 22a, 22b.

Figure 3:
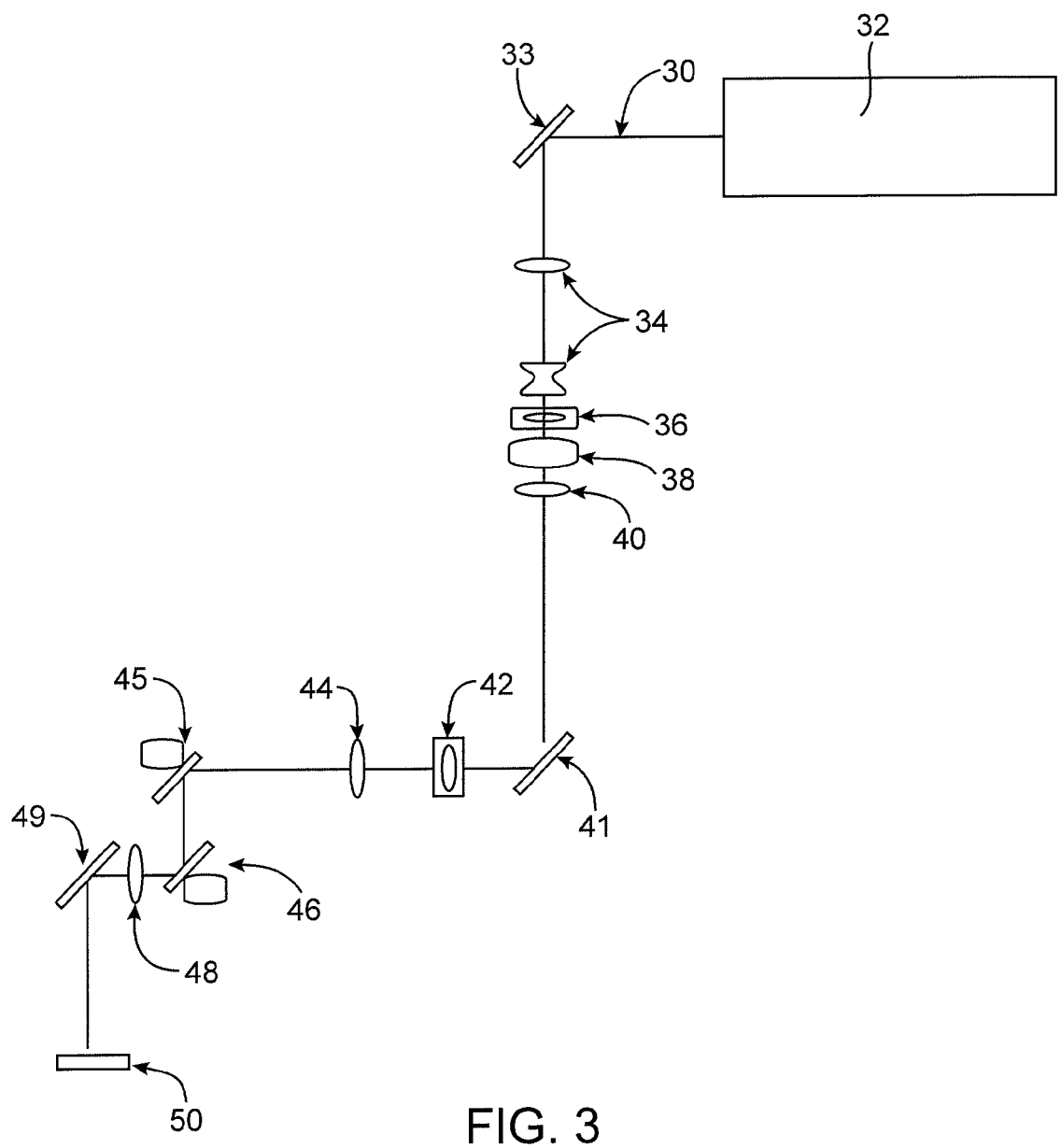
FIG. 3 is a schematic diagram of a laser beam optical delivery system incorporating one embodiment of the invention.

Referring now to FIG. 3, in one embodiment, a laser beam 30 is provided by a laser source 32 and directed toward a first mirror 33. The mirror 33 directs the beam 30 toward a sizing telescope 34, which sizes the beam 30 to a desired cross-sectional size. In one embodiment, for example, the cross sectional area of the sized beam 30 may be about 18 mm by about 20 mm. A lenslet aperture 36 is placed before the lenslet array 38 to size the beam 30 again, such as to create an 18 mm by 18 mm beam in one embodiment. The aperture 36 also aligned the beam 30 to the lenslet array 38 so as to fill the 16-lenslet, 4×4 grid. A positive power re-focusing lens 40 is placed after the lenslet array 38 to tilt the beamlets formed by the array 38 and to overlap the beamlets at an iris aperture 42, where the beamlets arrive after contacting another mirror 41. The beamlets may then pass through additional imaging lenses 44, 48 and mirrors 45, 46, 49, before reaching an ablation plane 50.

In one embodiment, the lenslet array 38 may be rotated about an axis between pulses of the laser beam 30. For example, the array 38 may be rotated approximately 45° away from the 0° and 90° angles relative to the axis of the laser beam 30. In some embodiments, the angles of rotation of the array 38 are within a window of 45°+/−10°, meaning between 35° and 55°. Rotation may occur in 90° increments between each pulse of a pulsed laser source 32, and with each rotation being within a window +/−10°. For example, angles of rotation could be about 45°, 135°, 225°, and 315°. Such rotation helps prevent formation of a laser beam having areas of striping or a grid pattern caused by the areas of the lenslet array 38 between lenslets. Rotation may be achieved via a drive mechanism coupled with the lenslet array 38 or via any other suitable means.

In some embodiments, the lenslet array 38 and the re-focusing lens 40 may be combined in one optic. This may be achieved, for example, by a lenslet array 38 having a gradual curvature along one or both of its opposed surfaces to give the lenslet array 38 an overall low positive power lens effect. Such a combined optic is adapted to split the laser beam 30 into multiple beamlets and also make the beamlets overlap in the plane of the aperture 42. In various embodiments, such a curved lenslet array 38 could be formed by programming lithography software to give a slight curvature to the optic or by disposing the partial cylindrical elements of the lenslet 38 on a curved substrate.

While the above provides a full and complete disclosure of the preferred embodiments of the invention, various modifications, alternate constructions and equivalents will occur to those skilled in the art. For example, while the invention has been described with express reference to an ophthalmological laser surgery system, other applications of the invention may be made, as desired. Therefore, the above should not be construed as limiting the invention, which is defined by the appended claims.

What is claimed is:

1. Apparatus for altering an energy distribution across a laser beam, the apparatus comprising:
   an array of optical power lenslets arranged in a pattern; and
   a structure to support the lenslet array with the lenslet array rotated in relation to two axes of the laser beam having an unequal divergence to account for coupling effects between the grid pattern and the two axes of the laser beam.

2. Apparatus as in claim 1, wherein the lenslet array comprises a square grid of at least 16 lenslets at least partially within the beam.

3. Apparatus as in claim 1, wherein the lenslet array comprises a hexagonal grid.

4. Apparatus as in claim 1, wherein the lenslet array comprises fused silica.

5. Apparatus as in claim 1, wherein the lenslet array comprises:
   a first side comprising a first linear array of concave cylindrical surfaces; and
   a second side opposite the first side and comprising a second linear array of concave cylindrical surfaces extending perpendicular to the surfaces of first linear array.

6. Apparatus as in claim 1, further comprising a drive for rotating the lenslet array about a longitudinal axis extending along the laser beam.

7. Apparatus as in claim 1, further comprising a re-focusing lens for directing the beamlets onto a target so that the beamlets overlap and the energy distribution is homogenized.

8. Apparatus for homogenizing an energy distribution across a laser beam, the apparatus comprising:
   a lenslet array for transmitting the laser beam as multiple beamlets, each lenslet having an effective optical power, wherein the lenslets are rotationally offset to account for coupling effects between a laser source and a geometry of the array.

9. Apparatus as in claim 8, further comprising at least one re-focusing lens for directing the beamlets onto a target so that the beamlets overlap and the energy distribution is homogenized.

10. Apparatus as in claim 9, wherein the lenslet array and the re-focusing lens are combined in one optic.

11. Apparatus as in claim 8, further comprising at least one rotating member for rotating the lenslet array about a longitudinal axis of the laser beam.

12. A system for providing a laser beam having a homogenized energy distribution to an eye of a patient, the system comprising:
   a source of laser energy to provide a pulsed laser beam with an unequal divergence in two axes;
   a lenslet array to transmit the laser beam as multiple beamlets, each lenslet having an effective optical power, the lenslet array comprising a pattern; and
   a mechanism to rotate the lenslet array about a longitudinal axis extending along the laser beam to rotationally offset the lenslet array and account for coupling of the unequal divergence in two axes of the laser beam with the pattern of the array.

13. A system as in claim 12, further comprising at least one focusing lens to direct the beamlets onto a target so that the beamlets overlap and the energy distribution is homogenized.

14. A system as in claim 12, wherein the system is configured to fire the laser when the lenslet array is rotationally offset.

15. A method for homogenizing an energy distribution across a laser beam, the method comprising:
   generating the laser beam with a laser, the laser beam comprising an unequal divergence in two axes; and
   passing a laser beam through a lenslet array having a pattern to transmit the laser beam as multiple beamlets, wherein the lenslet array is rotated about a longitudinal axis extending along the laser beam to account for coupling between the pattern and the unequal divergence of the two axes.

16. A method as in claim 15, further comprising directing the beamlets onto a target using at least one lens, so that the beamlets overlap and the energy distribution is homogenized.

17. A method as in claim 15, wherein the lenslet array comprises a negative power lenslet array, and wherein passing the beam through the lenslet array forms diverging beamlets.

18. A method as in claim 15, further comprising directing at least some of the beamlets through an aperture.

19. A method as in claim 18, wherein directing the beamlets through the aperture causes the beamlets to arrive collimated at an ablation plane.

20. A method as in claim 18, wherein a cross-sectional dimension of the aperture is selected to provide the laser beam with a desired cross-sectional dimension at an ablation plane.

\* \* \* \* \*